(12) United States Patent
Allan et al.

(10) Patent No.: US 6,252,131 B1
(45) Date of Patent: Jun. 26, 2001

(54) TRANSGENIC MAMMAL HAVING 5-HT3 TRANSGENE OVEREXPRESSION IN THE CMS

(75) Inventors: Andrea M. Allan, Albuquerque, NM (US); Sharon R. Engel, Winston-Salem, NC (US); Clifford R. Lyons, Albuquerque, NM (US)

(73) Assignee: University of New Mexico, Albuquerque, NM (US)

( * ) Notice: Subject to any disclaimer, the term of this patent is extended or adjusted under 35 U.S.C. 154(b) by 0 days.

(21) Appl. No.: 09/172,625

(22) Filed: Oct. 15, 1998

Related U.S. Application Data (60) Provisional application No. 60/061,847, filed on Oct. 15, 1997.

(51) Int. Cl.$^7$ .......................... A01K 67/027; C12N 5/00; C07H 21/02
(52) U.S. Cl. .................................... 800/18; 800/3; 800/8; 800/9; 800/21; 800/25; 435/320.1; 435/325; 435/455; 536/23.5
(58) Field of Search ................................. 800/21, 25, 14, 800/18, 3, 9; 536/23.5, 23.1, 24.5; 435/69.1, 320.1, 325, 455

(56) References Cited

U.S. PATENT DOCUMENTS 5,057,519  10/1991  Suberg ................................. 514/282

OTHER PUBLICATIONS

Eur. J. Pharmacol. 187:287–289, 1990.
Alcohol 9: 17–22.
Brain. Res. 513: 156–160, 1990.
Eur. J. Pharmacol. 164: 515–519, 1989.
Alcohol 26: 107–110, 1991.
Psychopharmacol. 112: 142–144, 1993.
Psychopharmacol. 112: 503–510, 1993.
Alcohol Clinic. Exp. Res. 18: 879–855, 1994.
Biol. Psch. 40: 514–421, 1996.
Maricq et al Science 254: 432–437, 1991.
Pharmacol. Biochem. Behavior 51; 835–842–1995.
Engel, et al, Psychopharmacology, 1998.
Wall RJ Theriogenology 45:57–68, 1996.*
Kappel et al. Current Opinion in Biotechnology 3:358–353 1992.*
Robert et al, Biol. Physchiatry 40:514–521, 1996.*

* cited by examiner

*Primary Examiner*—Deborah J. R. Clark
*Assistant Examiner*—Sumesh Kaushal
(74) *Attorney, Agent, or Firm*—Stephen A. Slusher; Nancy E. Ownbey (57) ABSTRACT

The invention relates to transgenic mammals characterized by 5-HT$_3$ receptor over-expression in the central nervous system (CNS). The mammals have particular utility as models for studying the role of 5-HT$_3$ receptors in the CNS, especially for the study of reward pathways for alcohol and other substances of abuse.

12 Claims, 5 Drawing Sheets

TRANSGENIC MAMMAL HAVING 5-HT3 TRANSGENE OVEREXPRESSION IN THE CNS

This application claims the benefit of Provisional application No. 60/061,847 filed Oct. 15, 1997.

BACKGROUND OF THE INVENTION

The invention relates to transgenic mammals characterized by $5\text{-}HT_3$ receptor over-expression in the central nervous system (CNS). In particular, the invention relates to such transgenic mammals having a significantly reduced desire for alcohol as compared to mice of the corresponding non-transgenic line.

1. Field of the Invention $5\text{-}HT_3$ receptors belong to a group of receptor subtypes for 5-hydroxytryptophan (serotonin). $5\text{-}HT_3$ receptors are primarily located presynaptically, and are known to modulate the release of a number of neurotransmitters, including GABA, acetylcholine, and dopamine. The receptors are ion-channel-coupled receptors, the only known receptors of this type in the serotonin family.

It is not yet clear how neurotransmitters such as serotonin regulate neuronal cell function. However, $5\text{-}HT_3$ receptors are believed to play a role in neurochemical reward pathways associated with the phenomena of drug abuse and other clinical conditions by modulating dopamine release in the mesolimbic pathway.

2. Discussion of Related Art

Many drugs of abuse, including alcohol, result in the release of dopamine in the nucleus accumbens of the brain, a region associated with motivation and reward. $5\text{-}HT_3$ receptor antagonists have been shown to cause a dose-dependent decrease in alcohol-stimulated dopamine release in the nucleus accumbens (*Eur. J. Pharmacol.* 87: 287–289, 1990; *Alcohol* 9: 17–22), and it appears that certain $5\text{-}HT_3$ agonists can stimulate dopamine release in the nucleus accumbens (*Brain Res.* 513: 156–160, 1990). Nicotine and opiates such as morphine also release dopamine in the nucleus accumbens, and this release can be blocked by $5\text{-}HT_3$ receptor antagonists (*Eur. J. Pharmacol.* 164: 515–519, 1989).

Animal studies have demonstrated that $5\text{-}HT_3$ receptor antagonists can decrease alcohol self-administration (*Alcohol* 26: 107–110, 1991; and others). In human studies, $5\text{-}HT_3$ receptor antagonists decreased pleasurable effects of alcohol and increased abstinence in mild alcoholics (*Psychopharmacol.* 112: 142–144, 1993; *Alcohol Clin. Exp Res.* 18: 879–855, 1994). Also, $5\text{-}HT_3$ antagonists enhanced the subjective feeling of intoxication produced by ethanol in at least one study (*Biol. Psychiatry* 40: 514–521, 1996).

$5\text{-}HT_3$ antagonists have been proposed for treatment of drug withdrawal syndromes, chemotherapy and drug-induced nausea and emesis, and as antimigraine, anxiolytic, and antipsychotic agents (reported in U.S. Pat. No. 5,057,519 to Suberg, et al.).

Studies of the $5\text{-}HT_3$ receptor have, however, been hampered by the low level of their normal expression in the CNS. $5\text{-}HT_3$ receptors are expressed throughout the forebrain in extremely low amounts. The highest amounts of $5\text{-}HT_3$ receptors appear to be present in the cingulate cortex, entorhinal cortex, hippocampus, and amygdala; the last has also been associated with drug abuse, but $5\text{-}HT_3$ receptors in this brain region have been less well characterized than those in the nucleus accumbens, where $5\text{-}HT_3$ receptors are particularly scarce.

SUMMARY OF THE DISCLOSURE

The inventions comprise transgenic mammals carrying an exogenous $5\text{-}HT_3$ transgene in their genome for over-expression in the CNS, particularly the forebrain. The inventions further comprise mammalian embryos carrying the $5\text{-}HT_3$ transgene capable of developing into viable transgenic animals whose progeny carry the transgene after breeding forward by sexual reproduction. The inventions additionally include DNA constructs comprising selected promoter+intron +$5\text{-}HT_3$ CDNA or DNA segments cloned into plasmids for ultimate insertion into the genome of a mammal.

The transgenic mammals of the invention are characterized by a high density of functional $5\text{-}HT_3$ receptors in the CNS of the mammals. They also exhibit a decreased desire for alcohol as compared to genetically similar non-transgenic mammals and decreased aggressiveness.

DETAILED DESCRIPTION OF THE INVENTION

Transgenic mammals according to the invention comprise mammals containing within their genomes endogenous $5\text{-}HT_3$ gene which naturally encode and express $5\text{-}HT_3$ receptors and further contain within their genomes at least one cDNA exogenous copy of this gene for over-expression of $5\text{-}HT_3$ receptors in the CNS of the transgenic mammals. The term 'docility' in the specification and claims shall be defined to encompas 'reduced agression,' and vice versa.

1. $5\text{-}HT_3$ Receptor Gene

The primary structure and functional expressions of certain $5\text{-}HT_3$ serotonin cell surface receptors are known and described, for example, in Maricq et al., *Science* 254: 432–437, 1991, incorporated herein by reference in its entirety. The nucleotide sequence encoding $5\text{-}HT_3$ receptor (5-HT$_3$R-A) according to this publication is deposited in GenBank under Accession No. M74425. The publication describes cDNA encoding mouse $5\text{-}HT_3$ receptor from cloned NCB-20 cells (a hybrid cell line derived from mouse neuroblastoma cells and Chinese hamster embryonic brain cells), which is useful in the practice of the present invention.

5-HT$_3$ nucleotide sequences from other mammalian sources including humans, comprising known and 5-HT$_3$ family members as yet to be discovered, are also useful as transgenes in the practice of this invention, provided the product transgenic mammal exhibits the characteristics described and claimed herein. The transgene(s) may be either homologous or heterologous with the starter mammals. Further, 5-HT$_3$ nucleotide sequences which have been truncated, for example to reduce potential immunogenicity of their encoded proteins expressed in heterologous species, may be employed with the proviso that the truncated sequence employed encodes and expresses functional 5-HT$_3$ receptor binding sites.

2. Engineering Constructs

DNA constructs comprising 5-HT$_3$ transgene(s) for production of the transgenic mammal of the invention typically also comprise selected nucleic acid regions associated with the transgene (as by fusion therewith) for mediation of, for example, its introduction into the target genome, its expression loci in the transgenic mammal, on/off external regulation of transgene expression, and other desired features, as generally known in the art. Inducible and tissue-specific promoters are exemplary.

The construct of the present invention is engineered to produce 5-HT3 over-expression substantially restricted to the CNS, especially the forebrain of the product transgenic mammal. One criticism of over-expressing transgenic mammals is that expression of the transgene not only occurs at sites where the native gene is expressed to obtain over-expression at these sites, but also is expressed in locations where the endogenous receptor is not expressed. The present invention obviates this predicted problem.

To obtain animal models according to the present invention which facilitate the study of the role of endogenous 5-HT$_3$ receptors in vivo, it is essential to limit over-expression of these receptors to endogenous binding site areas for 5-HT$_3$ receptor ligands and/or functional receptor expression sites, in particular, the central nervous system (CNS). 5-HT$_3$ receptors in the CNS have been identified in the enteric system, on sympathetic, para-sympathetic, and sensory nerve fibers in the CNS and on several mouse neuroblastoma lines. According to Maricq et al. (*Science*, ibid.), 5-HT$_3$ receptors are known to modulate intestinal contraction and transmission of pain sensations, but the function of 5-HT$_3$ receptors in the CNS remained obscure at the time of this publication.

In a particular embodiment of the invention, as exemplified below, a transgenic mammal is engineered to obtain 5-HT$_3$ over-expression restricted to the forebrain by controlling transgene expression with the tissue-specific Ca$^{2+}$ calmodulin (CAM) kinase IIα promoter. In this embodiment of the invention, no expression of 5-HT$_3$ receptors could be detected in the cerebellum or other body sites of the transgenic animals where 5-HT$_3$ receptor activity is not normally found in corresponding non-transgenic animals.

3. Utility of Products of the Invention.

The transgenic animal of this embodiment is thus an excellent model for studying the role of 5-HT$_3$ receptors in regulating dopamine release in the forebrain, particularly the nucleus accumbens, in various psychotropic diseases and conditions in addition to addictive or substance abuse disorders in which the presence or absence of dopamine is a significant factor, and in characterizing neuronal processes involved in these phenomena.

The product transgenic animal is particularly useful for the study of reward pathways for substances of abuse, as the nucleus accumbens and, more generally, the mesolimbic dopamine system are recognized as playing a major role in the rewarding properties of substances of abuse (*Pharmacol. Biochem. Behavior* 51: 835–842, 1995, incorporated herein by reference in its entirety).

The usefulness of this model is illustrated herein by a demonstration of the effect of 5-HT$_3$ over-expression in the forebrain on voluntary alcohol consumption. According to Campbell, et al. (*Pharmacol. Biochem. Behavior*, ibid.) 5-HT$_3$ receptors have a specific role in mediating dopamine release in the nucleus accumbens, and their data support the involvement of 5-HT$_3$ receptors in enhanced dopamine release in this region, suggesting prima facie that the normal high voluntary alcohol consumption in the founder strain (B6SJL) of the present transgenic mice before genetic alteration according to the invention is at least in part due to a natural increase in ethanol-stimulated, 5-HT3 modulated, dopamine release in pleasure pathways of the forebrain (see also Belknap et al. *Psychopharmacol.* 112: 503–510, 1993). Most unexpectedly, however, over-expression of 5-HT$_3$ receptors in these mice resulted in a marked decrease in ethanol consumption (see Examples).

The transgenic animals of the invention are accordingly useful inter alia for the development of pharmacotherapies for the treatment of substances of abuse which are positive modulators at 5-HT$_3$ receptors; for the development of 5-HT$_3$ receptor agonists or antagonists for clinical use or basic research; and as models for evaluating psychiatric conditions such as anxiety, aggression, or depression.

The exemplified transgenic mammal strains of the invention are very docile, as compared to the mammals prior to genetic altering (starter mammals), and are particularly suitable for the pet trade.

The invention is thus useful for imparting traits accompanying over-expression of 5-HT$_3$ receptors into a line or breed of mammals by genetically engineering one or more mammals of the line according to the invention to obtain transgenic mammals carrying at least one 5-HT$_3$ transgene in each of their genomes, which overexpress 5-HT$_3$ receptors in the CNS, preferably in the forebrain. Transgenic product mammals are then selected for desired traits and inbred into the line by assortative mating on the basis of phenotypic similarities as known in the art to promote homozygosity at the 5-HT$_3$ transgene locus.

Particularly contemplated for genetic intervention are lines or breeds of mammals that exhibit undesirable behavior such as aggressiveness or over-excitability, but that otherwise have highly desirable qualities, for example, exceptional show conformation, racing speed, herding or retrieving abilities, service work, or companionship. In such cases, the invention has particular veterinary or breeder use for imparting docility to the breed, while otherwise retaining the breed genotype.

4. Production of Transgenic Animals of the Invention

Specific methods of preparing the transgenic animals of the invention are described herein. However, numerous methods for preparing transgenic animals are now known in the art, and other methods will undoubtedly be developed. Any such methods which provide the 5-HT$_3$ over-expressing transgenic animals described herein can be used in the practice of the invention. The microinjection technique described herein is particularly suitable for addition of transgenes to the genome for over-expression without accompanying removal of other genes. An overview of techniques useful for engineering a transgenic mammal according to the present invention is set forth in U.S. Pat. No. 5,766,879 to Gerald et al. (incorporated herein by reference), who describe in some detail various general techniques and principles for engineering transgenic mammal expressing DNA encoding mammalian 5-HT$_4$ transgenic receptors.

The transgenic engineering processes described herein are generally believed to provide randomly altered genomes, and the transgenic products have not yet been genotyped. The transgenic mammals of the present invention are accordingly defined herein by phenotype, especially a characeristic high density expression of 5-HT$_3$ receptors, typically at least 100 fold greater density, in the forebrain and undetectable amounts thereof in the cerebellum, according to the binding experiments described in the Examples. Densities up to 2200 fmol receptor protein per mg of frontal cortex protein have been obtained; densities from about 1500 fmol and higher, particularly 2000 fmol and higher, are characteristic. The transgenic products are further characterized by their capacity to pass genetic over-expression of 5-HT$_3$ receptors to their progeny by normal breeding within selected strains of these animals. Strains described in the Examples (B6SJL, C57, DBA, and 129) have been identified for frozen embryo deposit with the American Type Culture Collection, Manassas, Va, USA, in conformance with the relevant provisions of the Budapest Treaty on the Deposits of Microorganisms for the Purpose of Patent Procedure, during the pendency of this or related applications.

5. Methods and Products Described in the Examples

The Examples describe the production of transgenic mice over-expressing 5-HT$_3$ receptors. The mice develop normally through adulthood and can pass the transgene to offspring by normal sexual reproduction. The 5-HT$_3$ receptors are over-expressed exclusively in the forebrain, with no increase in receptor or RNA being detected in cerebellum, liver, lung, heart, spleen, kidney, gut, testis, or skeletal muscle.

The $K_D$ values reported here (1.7 nM for transgenic mouse membranes and 2.4 nM for control mouse membranes) are comparable to those reported by other researchers for this ligand. In contrast, $B_{max}$ values for transgenic mice membranes (2.5 pmol/mg protein) are much higher than the values for control mice membranes (21 fmol/mg protein). The control membrane values are comparable to those reported by other researchers. Thus, cortical membranes from the transgenic mouse show approximately 100-fold increase in 5-HT$_3$ receptor binding sites in homogenates of whole cortical membrane, with no appreciable change in affinity of the receptor. 5-HT$_3$ receptor mRNA can be detected as early as embryonic day 10 in the rat and this receptor may play a role in secondary induction in fetal development, and early over-expression of 5-HT$_3$ receptors could compromise mouse development. Because the CAM kinase IIα protein is not highly expressed until after birth (Burgin et al., *J. Neuroscience* 10: 1788–1798, 1991), this promoter region ws used to limit the transgene expression until after birth, thereby limiting the interference of receptor over-expression during fetal development. Also, the transgenic 5-HT$_3$ receptor distribution in the forebrain closely resembles that reported for CAM kinase IIα protein. The CAM kinase IIα promotor region thus appears to have limited expression of the transgene to the forebrain where CAM kinase IIα is normally produced. Therefore, this promoter region is successful in limiting appreciable expression until after birth. Thus, it appears that this genetic manipulation has not disrupted normal mouse development.

The transgenic 5-HT$_3$ receptor appears to function the same as the endogenous receptor. Data to support this came from three types of experiments. First, ligand binding experiments in which an increased $B_{max}$ with no change in $K_D$ showed that more receptors were produced and that the receptor binding site binds ligand as does the endogenous receptor. The binding experiments were accomplished in washed membrane preparations which suggest that the receptor was incorporated into the plasma membrane as was the endogenous receptor. Second, electrical recordings of transgenic mice cells versus B6SJL/F1 controls showed an enhanced inward cationic current when stimulated with a 5-HT$_3$ agonist, demonstrating that the transgenic receptors formed functional ion channels in the membrane. Third, 5-HT$_3$ over-expression resulted in a behavioral change in the mice. The decrease in ethanol consumption by the transgenic mice reflects an alteration in the rewarding effects of ethanol for these mice due to 5-HT$_3$ receptor over-expression.

Gene insertion to produce the exemplified transgenic animals resulted in eight lines of mice being initially produced. Alcohol (ethanol) drinking behavior was tested in the four lines that showed over-expression of 5-HT$_3$ receptors by ligand binding (see below). The amount of ethanol consumption was related to the degree of 5-HT$_3$ over-expression (data not shown). The line that showed the least increase in receptor expression showed no statistical difference in ethanol consumption over control mice. However, the other three lines showed significant decrease in ethanol consumption over controls with the amount of receptor over-expression being inversely related to the amount of ethanol consumed. Thus, the transgene insertion locus alone is not responsible for the effect on ethanol consumption. The ethanol free choice test was used as one of the criteria for deciding which line would represent the best model in which to study the models and to breed forward onto the different inbred backgrounds (e.g., C57, DBA, 129 mice).

The following Examples illustrate the production of a transgenic mouse that over-expresses functional 5-HT$_3$ receptors on brain membranes in locations where the endogenous receptor is normally found. Furthermore, the over-expression of this receptor has produced behavioral changes that provide a useful model for testing hypotheses on the role of the 5-HT$_3$ receptor in alcohol abuse, and in other contexts.

EXAMPLES

I. Materials and Methods

Materials

3H-GR65630 was purchased from New England Nuclear (NEN). 32P was purchased from Amerham. (S)-Des-4-amino-3-[$^{125}$I]iodozacopride ($^{125}$I-DAIZAC) was a generous gift from Dr. William Hewlett (Vanderbilt University, Nashville, Tenn. USA). Tropisetron and MDL 72222 were purchased from Research Biochemicals International (RBI).

The DNA construct inserted into the mouse genome consisted of, from the 5'→3' direction, an 8.5 kbp region upstream of the CAM kinase IIα gene (CAM kinase IIα promoter region), an intron, and 5-HT$_3$ cDNA with its poly-A tail. CAM kinase IIα is not expressed in appreciable amounts until birth and its expression is limited to the forebrain. We used the CAM kinase IIα promoter region to limit 5-HT$_3$ receptor over-expression to the forebrain areas. The promoter region used was an 8.5 Kbp region upstream of the CAM kinase IIα gene. An additional intron was inserted to enhance transcription efficiency (Brinster et al., *Pro. Natl. Acad. Sci.* 85: 386, 840, 1988, and Wight and Wagner, *Mutation Research* 307: 420–440, 1994). 5-HT$_3$ cDNA was from NCB-20 cells (Maricq et al., *Science, op. cit.*, 1991). This is the long form of the receptor. What effect over-expression of this form over the short form has had in this animal model is unknown. The CAM kinase IIα sequence was isolated from a rat genomic library (Sunyer et al., *Proc. Natl. Acad. Sci.* 87: 278–282, 1990). Plasmids containing the CAM kinase IIα promoter region and intron were kindly provided by Dr. Mark Mayford (Columbia University, New York, N.Y., USA). 5-HT$_3$ cDNA plus its poly-A tail was from NCB-20 cells and kindly provided by Dr. David Julius (University of California, Los Angeles, Calif. USA). The CAM kinase IIα promoter, intron, and cDNA were ligated together and the 5'→3' sequence confirmed by restriction enzyme mapping, PCR and nucleotide sequencing. The total construct segment of promoter-intron-cDNA ~8500 bp+330 bp+2190 bp≡11 kbp) was purified with a Qiaex (Qiagen) purification column. Final size of the construct was ~11 kbp. This construct was inserted into the genome of B6SJL/F1 mice at the University of Alabama transgenic facility. Progeny were screened for the transgene by PCR to amplify a 500 bp region spanning the 3' end of the intron and the 5' end of the 5-HT$_3$ cDNA. Pups that were positive for the transgene by PCR were the founder mice for the 5-HT$_3$ transgenic mice lines.

Methods

Bacterial growth:

Bacterial growth media was 10 g/L Bacto-trypone, 5 g/l Bacto-yeast extract, 10 g/l NaCl, pH 7.5 with NaOH for liquid broth and 15 g/l agar from solid media. All cultures incorporated 50 µg/ml ampicillin except when growing pCDM6x1. When pCDM6x1 was grown up in MC1061/P3 cells the concentrations of ampicillin and tetracycline were 12.5 µg/ml and 7.5 µg/ml, respectively. Liquid cultures were grown overnight at 37° C. with rapid shaking (250 rpm) to ensure aeration of cells. Cultures grown on solid media were incubated from 1 to 2 days at 37° C.

Agarose gel electrophoresis:

Agarose gel electrophoresis was always carried out in 1% agarose in either TBE (0.089 M Tris, 0.089 M boric acid, 0.002 M EDTA) or TAE (0.04 M Tris-acetate, 001 M EDTA) and 0.5 µg/ml ethidium bromide. Gels were run at 3 to 5 V/cm unless otherwise stated. DNA markers were either λ HindIII (Gibco) or PCR marker (Sigma).

Transformation of cells with plasmid DNA:

Transformations of $E$ $coli$ cells or MC1061/P3 cells with plasmid DNA was by the method of Maniatis et al., $Proc.$ $Natl.$ $Acad.$ $Sci.$ 79: 4030–4034, 1982. Briefly, approximately $1 \times 10^8$ competent cells in 50 mM CaCl$_2$ 10mM tris, pH 8.0 were mixed with 3 to 10 µg plasmid DNA in a final volume of 0.1 ml and incubated 30 minutes at 4° C. DNA uptake was initiated by thermal shock at 42° C. for 3 minutes. Transformed cells containing the plasmid were grown in 1 ml liquid broth for 1 hour at 37° C. Single colonies were obtained by streaking solid media with 0.1 and 0.2 ml of the transformed cell mixture and incubating overnight.

DNA extraction and purification:

DNA purification was by phenol:CHCl$_3$ and ethanol precipitation. The DNA was extracted with an equal volume of a 1:1 phenol:CHCl$_3$. Ethanol precipitation was accomplished by adding a 0.1 volume of Na$^+$ acetate pH 5.0, followed by 2xvolumes of ethanol and the DNA pelleted by centrifugation in a microfuge (~10,000xg) for 10 to 15 minutes at room temperature or 4° C. At times the DNA was allowed to precipitate from 1 to 4 hours at −70° C. before centrifugation if the amount and size of the DNA was small.

DNA extraction from cells was either by STETL for small preparations (3 ml) or by Qiagen 500-tip columns (Qiagen) for larger cell preparations (500 ml). For small preparations, cells pelleted from 3 ml of liquid broth were suspended in 0.250 ml STETL (0.5 mg/ml lysozyme, 0.5% triton x100, 8% sucrose, 50 mM tris, 50 mM EDTA, pH 8.0) and boiled for 30 seconds followed by centrifugation at 10,000xg for 15 minutes at 40°. The pellet was removed with a toothpick and the plasmid precipitated from the supernate with an equal volume of isopropanol. The DNA was suspended in 10µl water and either 5 µl used in restriction enzyme mapping or 2 µl used as template in PCR reaction. The Qiagen kit uses (as final concentrations) 133 mM NAOH, 0.67% sodium dodocal sulfate (SDS), and 33 µg/ml RNAase in 16.7 mM tris pH 8.0, 3.33 mM EDTA for cell lysis and RNA elimination. After neutralization with 3 M K$^+$ acetate pH 5.5, the protein pellet and cell debris was removed by centrifugation (10,000xg 15 min 4° C.). The supernatant containing the plasmid DNA is applied to the Qiagen column and the plasmid DNA eluted with 1.25 M NaCl in 50 mM tris, pH 8.5 and 15% ethanol.

DNA extraction from agarose gels was achieved by spinning through glass wool or with either QIA Quick or QUIEXII gel extraction kits (Qiagen). For the glass wool method, the slice of gel containing the DNA band of interest was spun through a small amount of glass wool lining a 0.5 ml microfuge tube with a hole punched in the bottom of the tube, and the fluid from the gel containing the DNA collected into a 1.5 ml tube by centrifugation for 10 min at ~10,000xg at room temperature. The QIA Quick and QUIEXII gel extraction kits (Qiagen) used a patented solubilization buffer to dissolve a DNA containing slice of agarose gel and the plasmid DNA is separated from contaminates using a patented column.

Ligation reactions:

Ligation reactions consisted of a 1:4 to 6 ratio of vector-:insert DNA, in 50 mM tris pH 7.4, 10 mM MgC$_2$ 10 mM dithiothreitol, 1 mM spermidine, 1 mM ATP, 0.1 mg/ml BSA, 10 U/µg vector DNA T$_4$ ligase (Gibco) in a final volume of 20 µl. Reactions were carried out at 15 or 16° C. overnight.

Production of blunt ends:

Klenow reactions were carried out for 30 minutes at room temperature with 1 µl (≧2 U/µg DNA) Klenow (Gibco), 0.25 mM dNTP's, in 10 mM tris pH 8.0,10 mM NaCl, 2 mM MgC$_{12}$, and 5 to 10 µg DNA.

Polymerase chain reactions (PCR):

All PCR reactions, unless otherwise stated, were run with between 20–100 µg template DNA, 0.2 pmoles/reaction of each primer, 200 µM dNTP's, and 1 Unit/ TAQ polymerase 50 µl reaction in PCR buffer (10 mM tris, 50 mM KCl, 1.5 mM MgCl, pH 8.3). Unless otherwise stated, PCR reaction protocol was as follows: DNA template was denatured by heating at 94° C. for 3 minutes, then 35 cycles of denaturation (94° C. for 5 seconds), annealing of primers (65° C. for 1 minute), and nucleotide extension (7220 C. for 1 minute).

Extraction of DNA from mice tails:

After weaning mice were ear tagged. One cm of the tip of the mouse tail was removed with scissors and bleeding stopped with silver-nitrate sticks. The cm of tail was digested with 1 ml of 0.2 mg/ml proteinase K and 0.5% SDS in 10 mM tri pH 8.0, 100 mM NaCl, and 50 mM EDTA at 55° C. overnight with shaking. Genomic DNA was first extracted with 1 ml of a 1:1 phenol:CHCl$_3$ equilibrated to pH 8.0. After centrifugation at 6,500xg for 30 min at 4° C., 0.8 ml of the aqueous phase was extracted again with 0.5 ml CHCl$_3$. Phase separation was accomplished by centrifugation at 10,000xg for 3 min and 0.7 ml of the aqueous phase mixed with 0.8 ml ethanol. Precipitated DNA was pelleted by centrifugation at 10,000xg 1 min and the DNA allowed to hydrate in water or TE 1 mM tris pH 8.0, 1 mM EDTA overnight.

Southerns:

10 µg of genomic DNA was cut with 1 to 3 U/µg DNA either EcoRV, Bam H1,or HindIII at 37° C. for 3 hours or overnight. DNA fragments were extracted with phenol:CHCl$_3$, precipitated with ethanol, and DNA suspended in water of TE. Fragments were separated by electrophoresis on a 1% agarose gel. After band separation, the fragments were depurinated by soaking the gel in 0.25 M HCl for 10 minutes to nick larger pieces of DNA for more efficient transfer. The fragments were then denatured by soaking the gel in 0.5 M NaOH, 1.5 M NaCl, for 30 minutes followed by neutralization by soaking the gel in 1.5 m NaCl, 0.5 M tris pH 7.0 for 30 minutes. The fragments were transferred to a positively charged nylon membrane (GeneScreen, NENO in 10 × SSC (20 × SSC is 3 M NaCl, 0.3 M Na$_3$-citrate pH 7.0) for 1.5 hours under 4 inches Hg vacuum pressure. DNA was attached to the membrane by cross-linking with 120 mj. Unbound sites on the membrane was blocked by pre-hybridizing in 5 × SSC, 5 × Denhardts solution (0.1% ficoll 400, 0.1% polyvinylpyrrolidone, land 0.1% BSA final concentrations. 1% SDS, and 100 $\mu$g/ml sheared salmon sperm DNA at 65°C. overnight. An $\alpha$-$^{32}$P-dCP containing probe that corresponds to 800 bp of the 5-HT$_3$ DNA was prepared by random priming (Gibco random priming kit) and was added to the pre-hybridizing solution at 1,000,000 cpm/ml and hybridized overnight at 65° C. The amount of pre-hybridizing and hybridizing solutions used were 0.5 to 1 ml/ 10 cm$^2$ membrane. Unhybridized probe was removed by washing the membrane twice in 2 × SSC/0.1% SDS at 65° C. for 30 min and with washes of 0.2 × SSC/0.1% SDS 65° C. for 30 minutes. The membrane was then exposed to BioMaxMS (Kodak) film for 1–2 days at −700° C.

Cloning of the construct:

The intron was supplied in a plasmid designated as PNN265 and came with a complete map (Mark Mayford, Columbia University, New York, N.Y., USA). The CAM kinase II$\alpha$ promoter was supplied in plasmid called pmm403 and came with a limited map. Both of these plasmids contained an ampicillin resistance gene. 5-HT$_3$ cDNA was supplied in the pCDM6×1 plasmid and also came with a limited map. The pCDM6×1 plasmid requires the helper P3 plasmid for ampicillin and tetracycline resistance to be activated. All plasmids, PNN265, pmm403, and pCDM6×1, were grown in maxi-preps of 500 ml liquid broth. Plasmid DNA was extracted and purified by using a Qiagen-tip 500 column (Qiagen). Plasmids were subjected to electrophoresis on an agarose gel along side DNA markers to confirm their appropriate size. Molecular weights of the plasmids coincided with their accompanying maps: PNN265 ≈ 5163, pmm403 ≈ 10,500 bp, and pCDM6×1 ≈ 4000 bp. The following references, incorporated herein by reference discuss the intron and plasmid used here: Mayford, et al., *Cold Spring Harbor Symposia on Ouantitative Biology* 61: 219–224, 1996; Mayford, et al. *J. Neurochem.* 66: 531, 1996; Jz, et al. *Cell* 87: 1316–1326, 1996; Rotenberg, et al., *Cell* 87: 1351–1361, 1996; Mayford, et al. *Current Biol.* 7: R580–R589, 1997; Mayford, et al. *Science* 274: 1678–1683, 1996; Mayford *Proc. Natl. Acad. Sci. USA*, 93: 13250–13255, 1996.

The overall goal was to clone the 5-HT$_3$ cDNA from pCDM6×1 3' to the intron in PNN265, remove the intron +cDNA from PNN265, and clone that segment 3' to the CAM kinase II$\alpha$ promoter in pmm403; followed by removing the CAM kinase II$\alpha$ promoter + intron + 5-HT$_3$ cDNA segment from pmm403 for insertion into a mouse genome by micro-injection.

Two strategies were initiated to get the 5-HT$_3$ cDNA 3' to the intron. One strategy was to use PCR to amplify the gene from pCDM6×1 using primers that would create a BglII site at both ends of the cDNA and ligate into the BglII site of PNN265 that is just 3' of the intron. A second strategy was to cut the existing 5-HT$_3$ cDNA from pCDM6×1 and use a blunt end ligation reaction into the EcoRV site of PNN265 that was also just of the intron. The advantage of the BglII approach is that it is a more efficient ligation reaction than using blunt ends. The disadvantage of the BglII method is that the PCR amplification could introduce point mutations into the cDNA segment. The disadvantage of the second approach is the inefficient blunt end ligation and its advantage is that there is no amplification step. The cloning step was accomplished here by the second method more quickly than by the BglII method. The BglII method never worked very well. We believe that there was a problem with too short of ends for BglII to cut from or else the BglII primers were not the correct sequence. As the other method was working we did not investigate this problem further.

The concentrations of PNN265 and pCDM6×1 were estimated by optical density (O.D.) Using the formula of 50 $\mu$g/ml/O.D.$_{260mm}$. An ~2,000 bp segment containing the 5-HT$_3$ cDNA was removed from 10$\mu$g of pCDM6×1 with Xbal. PNN265 (5$\mu$g) was linearized with EcoRV. Both reactions were treated with Klenow enzyme to fill in nucleotides on over-hanging 3' ends to form blunt ends. DNA segments were then purified by extraction with phenol:CHCl$_3$ and ethanol precipitation. After suspension in water, the fragments were separated on a 1% agarose gel at 1 volt/cm. Bands of the appropriate size were cut out from the gel with a razor blade and spin through a small amount of glass wool for 10 minutes in a microfuge to collect the DNA. The eluted DNA was purified by extraction with phenol:CHCl$_3$ precipitated with ethanol, and suspended in 10$\mu$l water. The PNN265 linearized DNA and 5-HT$_3$ cDNA were ligated together by blunt end litigation. One-half of the ligation mixture was then used to transform competent *E. coli* cells and the transformed bacteria was plated to obtain single colonies on ampicillin containing media. Colonies were allowed to grow overnight at 37° C.

Single colonies were selected with a toothpick and presence of the 5-HT$_3$ cDNA was checked by amplifying a 469 bp region of the 5-HT$_3$ DNA using a primer directed to the internal part of the cDNA (mid 5' primer) and to the 3' end of the cDNA (3' serotonin gene primer). Colonies that were positive for the 5-HT$_3$ gene were grown in 4 ml of liquid broth plus ampicillin. Plasmids were collected from these cells by boiling in STETL. The direction of insertion of the 5-HT$_3$ cDNA relative to the intron was checked by 3 methods: restriction enzyme mapping, PCR, and DNA sequencing.

Restriction enzyme mapping was done 3 times. The first map was with HindIII cut PNN265 at 2964 and 3240 and cut 5-HT$_3$ cDNA once at 51 bp from the 5' end. For a 5'→3' insertion the length of fragments would be 6512, 276 and 175 bps and for 3'→5' direction 276, 1873, and 4814 bps. After 6 ligation reactions and initial restriction enzyme checks, 3 colonies appeared to have a banding pattern to suggest 5'→3' insertion. A second restriction enzyme map was constructed using SmaI and BglII. BglII cuts PNN265 once at 3263 and SmaI cuts 5-HT$_3$ cDNA once at 118, so for a 5'→3' directional insert the fragments would be 219 and 6744 and for a 3'→5' directional insertion the fragments would be 1783 and 5180. Two colonies had a banding patten resembling a 5'→3' insertion. The third restriction mapped used KPN which cut PNN265 at 2974 and 4207 and cut 5-HT$_3$ cDNA at 329 and 973. For a 5'→3' direction, the fragment would be 644, 719, 1670, and 3930 bp's. For a 3'→5' direction the fragments would be 644, 1172, 1217, and 3930 bp's. For PNN265 without any cDNA the fragments would be 1233 and 3930 bp's. Only DNA from colony #3 had a banding pattern that was consistent with a 5'→3' direction.

PCR was used to check for 5-HT$_3$ cDNA insertion into PNN265 by amplifying the full length cDNA insert (~2000 bp) product using primers designed to anneal to the 5' end of the cDNA and 3' end of the cDNA. Only plasmid DNA from colony #3 was able to produce a 2000 bp product using these primers.

Sequencing (Sequenase kit, United States Biochemical) was used to check for insertion of 5-HT$_3$ cDNA into PNN265 and to confirm that a poly-A tail was included with the 5-HT$_3$ cDNA. A primer 5' to the cDNA was designed to sequence, in the 3'→5' direction from the 5' end of the cDNA into the intron in PNN265. Another primer was used to sequence in the 5'→3' direction form the 3' end of the cDNA into its own poly-A tail. Sequencing was accomplished per manufacturers instructions, briefly, 0.5 µg primer was annealed to 3.5 µg denatured template (PNN265+cDNA insert). Denaturization of template was accomplished by exposing the template DNA to 0.2 M NaOH containing 0.2 mM EDTA for 30 minutes at 37° C. The label was $\alpha$-$^{35}$S-ATP and reactions were stopped with ddNTP's. Sequenced fragments were separated on a 6% polyacrylamide gel. The gel was dried onto Whatman 3MM paper and film exposed 18 hours at -70° C.

Using this strategy a poly-A tail 3' of the 5-HT$_3$ cDNA was confirmed and the sequence of 267 bases of PNN265 5' to the 5-HT3 cDNA was identified. Eight different restriction enzyme cutting sites in PNN265 were identified from the sequence that corresponded to the map that accompanied the PNN265 plasmid.

Once the presence of 5-HT$_3$ cDNA plus its poly-A tail in the 5'→3' direction was confirmed, the intron plus cDNA segment was removed from PNN265 with NotI. NotI cuts PNN265 at 3040 and 4483 but not the cDNA. However there was a NotI site just after the 5-HT$_3$ cDNA plus its poly-A tail and 5' of the XbaI site in cPDM6×1 so that the poly-A tail that was in PNN265 was not incorporated into the construct. Three fragments were obtained from a NotI cut: 1119, 2124 (containing the intron and 5-HT$_3$ cDNA), and 3720 bp.

Pmm403 was linearized with NotI and treated with calf intestinal phosphatase (CIP) at ≧0.1 U/µg DNA for 30 minutes at 37° C. to cleave the terminal phosphate groups. This procedure reduces the likelihood of ligating the two ends of pmm403 together rather than with the cDNA insert. The linearized pmm403 and PNN265+ cDNA insert NotI fragments were separated on an agarose gel and the bands corresponding to the linear pmm403 and intron+cDNA (2124 bp) fragment from PNN265 removed with a razor. The DNA fragments were purified from the gel with a QIAQuick extraction column (Qiagen). Ligation of linearized pmm403 and the 2124 bp NotI fragment was carried out overnight at 14° C. Competent *E. coli* cells were transformed with the ligation mixture and plates streaked for single colonies on ampicillin media. Single colonies were screened for the presence of the 5-HT$_3$ cDNA by PCR.

Restriction enzyme mapping with HindIII and NotI and PCR were used to confirm 5'→3' direction. NotI was used to remove the ~2,000 bp fragment from the vector to confirm the presence of a NotI sensitive site that held an appropriate size fragment. HindIII cut the PNN265 insert twice and pmm403 once. A 5'→3' directional insert would give three fragments of 8500, 3000, and 175 bp's and a 3'→5' insert direction would give 10,500, 3,000, and 175 bp fragments. DNA from colonies 1 and 6 have restriction enzyme fragments consistent with a 5'→3' insert.

A second check of insertion was accomplished using a primer directed towards the 3' end of the CAM kinase IIα promoter (5' CAM primer) and a primer directed at the 5' end of the 5-HT$_3$ cDNA (3' gene primer) to amplify a 1,000 bp fragment between the CAM kinase IIα promoter and the 5-HT$_3$ cDNA (5' intron primer) and the 3' gene primer were used to amplify a 500 bp fragment between the intron and the 5-HT$_3$ cDNA. Using this strategy the presence of the intron-cDNA and the promoter cDNA segments in the 5'→3' direction was confirmed.

The promoter-intron-5-HT$_3$ cDNA segment could be removed from the pmm403 plasmid with Sfil or Srf. Efforts to remove this segment with Sfil were unsuccessful. Apparently, a Sfil site was introduced in the pCDM6×1 plasmid, resulting in additional fragments being generated with this enzyme.

Srf was then tried and was able to remove the construct from pmm403. The construct comprises an 8,500 bp promoter, and a 2,500 bp region containing the intron and 5-HT$_3$ cDNA. The total size of the construct was 11,500 bp. The Srf generated fragments were separated on an agarose gel and the construct removed with a razor blade. The construct was purified from the gel with the QIAEXII column (Qiagen). Gel electrophoresis (1% agarose) of 150 ng and 500 ng of the construct DNA showed it to be a single band.

It took 6 ligation reactions to get the 5-HT$_3$ cDNA into the PNN265 vector in the 5'→3' direction and 3 ligation reactions to get the intron plus 5-HT$_3$ cDNA into the pmm403 plasmid in the 5'→3' direction.

B6SJL/F1 mouse tail DNA (1 cm) was digested with SDS and proteinase K overnight at 55°C. 20 ng of tail DNA was spiked with the construct to equate to 1, 5, and 10 copies of the construct per cell. PCR reactions using the 5' intron and 3' gene primers was used to amplify a 500 bp fragment from the equivalent amount of DNA as would be found in 1, 5, and 10 copies/cell alone and in 20 ng of B6SJL//F1 tail DNA. The formula used to calculate one copy per cell was: (1 copy/cell) (11,000 bp/copy) (1 cell/6×10$^9$ bp) (20 ng tail DNA)=37 fg construct. We were able to detect down to 1 copy per cell with the PCR reaction; the presence of the B6SJL/F1 tail DNA had no effect of the PCR reaction. The B6SJL/F1 mouse DNA did not cross-react with the primers used.

Micro-injection of the construct and production of 5-HT$_3$ transgenic mice:

3 µg contract DNA plus the 5' intron and 3' gene primers were sent to the University of Alabama Transgenic Mouse Development Facility for micro-injection of the DNA. 175 eggs were injected with the construct at the University of Alabama (UAB) on Jun. 28, 1996 and of these, 157 survived and were implanted into 6 female mice. On Jul. 16, 1996, 44 live mice and one dead mouse was born from these implantations. Thirty tails from these mice were analyzed for the gene inserted by PCR using the 5' intron and 3' gene primers at the UAB facility. Five positive mice were identified and sent to the University of New Mexico (UNM) along with the remaining 14 unanalyzed mice. The remaining mice were analyzed by the same method and an additional 3 transgenic mice were identified. One of the 5 transgenic mice analyzed at the UAB died in transport to UNM. The total number of transgenic mice produced was 8. After the one death, there remained 7 lines of transgenic mice. The lines were designated by the ear tag number assigned to the founder mouse. The lines are 2, 10, 13, 15, 16, 17, and 18.

Breeding of transgenic mice:

The 5-HT$_3$ transgenic mice were crossed with non-transgenic B6SJL/F1 mice and the prodigy checked for the transgene by PCR. After the first cross to the non-transgenic B6SJL/F1 mouse, the transgenic mice were subjected to brother-sister mating within each line to produce mice homozygous (+/+) for the transgene in each line. Once an adequate colony of mice was obtained, mice which were able to over-express the transgene were identified by ligand binding studies.

Two lines of mice, lines 2 and 17, were unable to pass the transgene to their offspring. Both of these mice were males. These mice were able to reproduce and repeated PCR reactions showed an amplified product, however, the reaction only resulted in medium to faint bands. Line 2 produced only one PCR positive pup (also a male) out of a total of 52 pups fathered. This single line 2 descendent was also not able to pass the transgene forward even after multiple litters with different females and the PCR product was also faint. After several tries at breeding these lines forward, they were eliminated. Line 17 fathered a total of 30 pups without a single pup being PCR positive for the transgene. It would appear that the transgene insertion site for these two lines was such that inheritance of the transgene was lethal, possibly due to the disruption of another gene. This does not explain why the two founders were able to survive nor how the single line 2 descendent was able to survive. Regardless of the molecular mechanism acting in these two lines, since they were unable to pass the transgene forward, they were not useful candidates for a mouse model of $5$-$HT_3$ receptor function drug abuse. Hence, lines 2 and 17 were destroyed and no further investigation into these animals was undertaken.

Southern analysis of transgenic mice:

The probe was designed so that when the DNA was digested with EcoRV, the endogenous and transgene could be easily identified. EcoRV cuts the $5$-$HT_3$ cDNA at 744 and 1745 bases (bases numbered according to the gene bank sequence for the mouse $5$-$HT_3$ receptor assession No. M74425). Within the segment cut by EcoRV are 3 introns in the endogenous gene (Utez, et al., Febs Letters 339: 302–306, 1994):introns 6(331 bp) at base 778 , intron 7(9 bp) at base 985, and intron 8(564–582 bp) at base 1207. This segment also contains the alternative slice site for 18 bases between bases 1208 and 1227. The probe was designed to label a segment between bases 841 to 1629 (1008 bp). Therefore the endogenous gene should be on a segment that is, assuming mostly short form and assuming that EcoRV does not cut within these intron segments, 1008+331+91+(564−582)−~=1976=1994 bp≈2000 bp and the transgene should be on a segment that is 1008≈1000 bp.

Southern analysis of tail DNA (10$\mu$g) from lines 10, 13, 15 and non-transgenic B6SJL/F1 (control) mice cut with EcoRV allowed the visualization of the transgene in lines 10, 13, 15, and 16 corresponding to an approximately 1,000 bp segment and the endogenous gene in lines 10, 13, 15, 16, and control mice corresponding at an approximately 2,000 bp segment. Some additional bands can be seen at large molecular weights (line 15 lane for example). These probably represent partial digestion with EcoRV. In the lane for line 10 there is an additional band just above the 2,000 bp mark that seems too prominent and small to represent a partial digest. However, this could not represent an additional insertion site, such as on another chromosome, because EcoRV should still remove the 1008 bp segment from within the cDNA insert.

Although an estimate of 10$\mu$g of DNA was initially cut for all animals, ethidium bromide staining of the gel prior to transfer of DNA to the membrane, revealed that actual amounts of DNA on the gel were not equal. The DNA concentrations were calculated from O.D. values. The large nature of the genomic DNA molecules makes accurate calculation of DNA difficult. The lanes containing DNA from heterozygote(+/−) transgenic animals (lines 10, 13, 15, and 16) and control appear to have approximately similar amounts of DNA as estimated from the ethidium bromide staining. If that is true, then the increasing density of the transgene lanes can be interpreted as an increase in gene dosing. The heterozygous (+/+) lanes for all transgenic lines were barely detectable by ethidium bromide staining, but also appear to contain similar amounts of total DNA. Looking at the density of probe binding between the transgenic lines for either (++) or (+/−) lanes, it appears that the highest gene dose is in line 15 followed next by line 13. Line 10 and 16 appear to have similar gene doses that are less than line 13.

BamHI was used to check for additional insertion sites of the transgene. BamHI cuts the CAM kinase II$\mu$promoter region but not the $5$-$HT_3$ CDNA. It is unknown whether the introns of the endogenous $5$-$HT_3$ receptor are cut by this enzyme. However, because this enzyme will cut the promoter region of the transgene, digestion with BamHI results in the endogenous and transgene being on different length segments of DNA.

BamHI digest results were compared for line 13, line 15, and a control mouse. In the control lane the endogenous gene was seen at a high molecular weight. Ethidium bromide staining revealed that very little DNA was loaded onto the line 13 and line 15 lanes; however, in line 15 a faint band corresponding to the endogenous gene and another heavily stained band corresponding to the transgene was seen. Line 13 only showed the transgene, probably due to the small amount of DNA loaded onto the gel. (Results not shown.)

DNA from the current breeders for line 13 and controls was cut with HindII to further assess multiple insertion sites of transgene. Ethidium bromide staining revealed that approximate amounts of DNA were loaded on to the gel from each sample. It appears that HindIII did not cut the DNA into many segments however, no clear multiple banding pattern is visible suggesting that there is only a single insertion site for the transgene.

Receptor binding

For homogenate binding studies, cortices and cerebelli were removed and homogenized by hand in ice cold Hepes buffer (50 mM, pH 7.5) and centrifuged at 500 g for 5 minutes at 4° C. Liver, lung, heart, spleen, kidney, small intestines, testes, and skeletal muscle (from hind limb) were homogenized with an Omni tissue chopper. Membranes were pelleted by centrifugation at 20,000 g for 20 minutes at 4° C. and the pellets washed twice before suspension to 3 mg/ml in a buffer containing 145 mM NaCl, 5 mM KCl, 1 mM $MgCl_2$, 1 mM $CaCl_2$, 10 mM glucose, and 10 mM TRIS, pH 7.5. Saturation curves were carried out with 0.0125-25 nM $^3$H-GR65630 at 37° C. for 30 minutes with 300 $\mu$g total protein. Incubation was terminated by dilution with x10 volume (5 ml) of ice-cold buffer followed by rapid filtration onto Whatman GF/B filters. Filters were washed twice with 5 ml ice-cold buffer and counted by scintillation counting in EcoLite (ICN) scintillation cocktail. Non-specific binding (NSB) was determined with 0.125-256 $\mu$M tropisetron. Displacement binding was carried out the same as saturation binding except with 1 nM $^3$H-GR65630 and NSB defined with 10 $\mu$M tropisetron. Protein concentrations were determined by Folin phenol reagent (Lowry et al., J. Biol. Chem. 193: 256–275, 1951).

Localization of receptor over-expression in the CNS was accomplished in brain slices using an iodinated $5$-$HT_3$ antagonist, $^{125}$I-DAIZAC (Mason et al. 1996). Brains were removed on ice, frozen in isopentane, and stored at −70° C. until use. Sections (10 μm thick) were sliced at −20° C. and thaw-mounted onto SuperFrost Plus (Eier Scientific) slides. Binding assays of slices were performed at room temperature in 50 mM Hepes, 5 mM CaCl$_2$, 2.4 mM MgCl$_2$, pH 7.6. NSB was defined by 4 μM MDL 72222. Sections were pre-incubated for 30 minutes, incubated in $^{251}$I-DAIZAC for 60 minutes, and washed twice in ice-cold buffer for 1 minute followed by a 1 minute rinse in ice cold water. Sections were dried under a stream of air and BioMax-MS (Kodak) film exposed for 12–24 hours.

Northern analysis

Tissues were homogenized with the Omni tissue chopper in TRIzol (Gibco) and RNA extracted by CHCl$_3$ phase separation and ethanol precipitation. Total RNA (20 μg and 40 μg per well) was separated on a 2.0 M formaldehyde/1% agarose gel. Confirmation of intact RNA was by visualizing the 28 s and 18 S RNA bands with ethidium bromide staining. RNA was transferred to GeneScreen Plus (NEN) membrane and remaining sites on the membrane bound with 0.1 mg/ml salmon sperm DNA (Gibco) in 50% formamide. 5×SSC (20×SSC is 3 M NaCl, 0.3 M Na$^+$, pH 7.0), 5 Denhardt's solution (0.1% Ficoll, 0.1% bovine serum albumin, 0.1% polyvinylpyrrolidone), and 1% SDS. The membrane was then incubated with a $^{32}$P-labeled probe made by random priming (Gibco Random Primers DNA Labeling System) of an 800 bp region of the 5-HT$_3$ cDNA in the same buffer at 42° C. overnight. Unbound protein was removed by washing the membrane twice with 2×SSC/0.1% SDS for 30 minutes at 65° C. and twice with 0.2×SSC/0.1% SDS for 30 minutes at 65°C. The band of 5-HT$_3$ RNA was visualized by exposing BioMax-MS (Kodak) film at −70° C. for 2–4 days.

Ethanol consumption

Mice were housed individually and subjected to a two-bottle choice test in which the mice were offered 10% (wt/vol) ethanol in H$_2$O in one bottle and H$_2$O in another bottle. Bottles (50 ml) equipped with balled-sipper tubes were used to limit loss of fluid by evaporation and dripping. The position of the tubes was switched daily to avoid a place bias. Fresh ethanol and water were prepared and weighed daily. Data were collected for 10 days and then the mean g/kg ethanol consumed daily calculated. Mice were weighed before and at the end of the experiment to check for weight loss.

Animals

All procedures involving animals were approved by the Animal Care and Use Committee at the University of New Mexico and in according with NIH guidelines in "Principles of laboratory animal care" (publication No. 85-23). Mice were bred and maintained in a controlled environment in the university's vivarium on a 12-hour light:dark cycle with food and water ad libitum. All mice were between the ages of 90–120 days.

II. Summary of Results

Production of 5-HT3 transgenic mice

Figure 1:
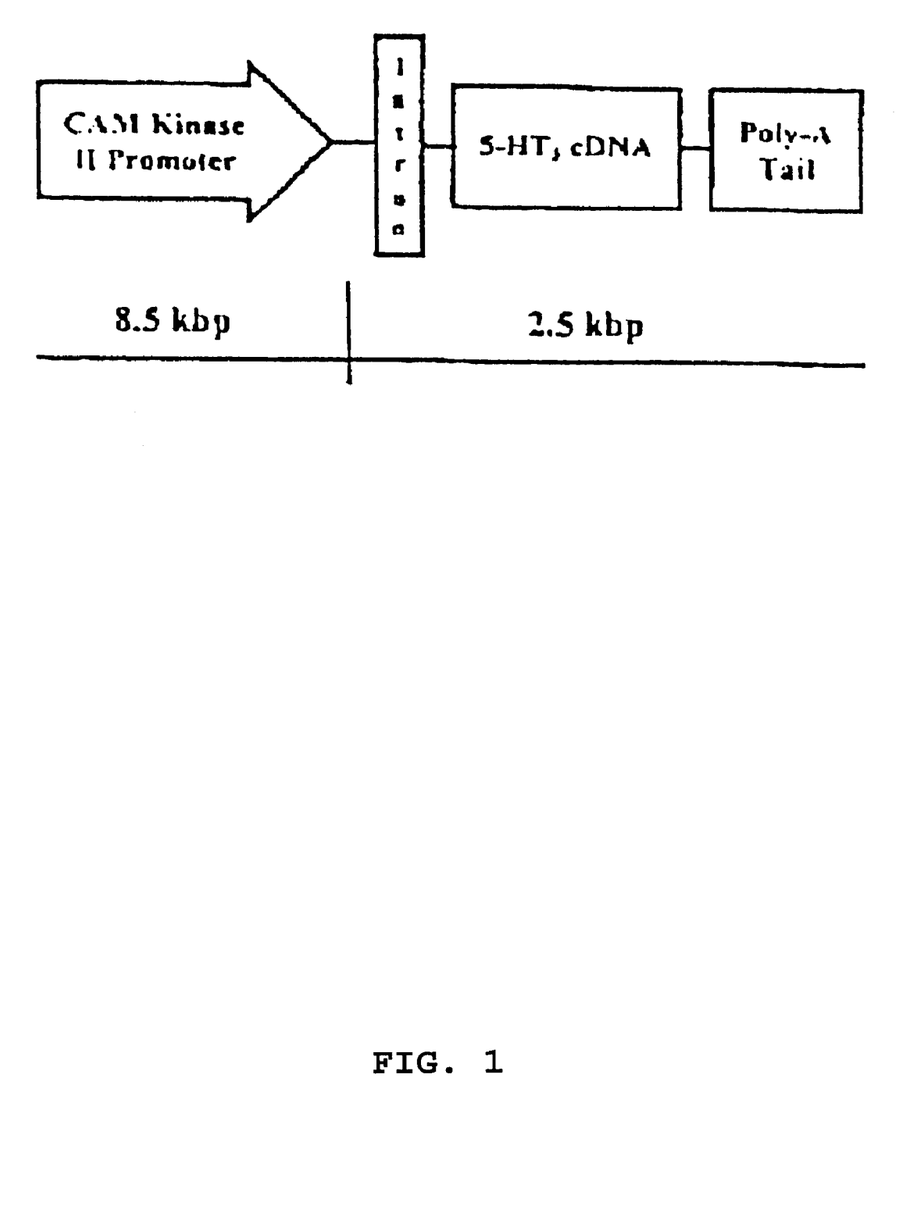
FIG. 1 shows a 5-HT3 transgene construct consisting of 8.5 kbp upstream region of the CAM kinase IIα gene. 330 bp intron, 2190 $5\text{-}HT_3$ cDNA plus poly-A tail. Total size ~ 11 kbp.

One hundred and seventy-five embryos were microinjected with the 5-HT$_3$ gene construct (FIG. 1) and 44 live pups were produced. Transgene insertion was confirmed by amplifying a 500 bp segment of DNA from the 3' end of the intron and the 5' end of the 5-HT$_3$ cDNA. Of the 44 live births, eight pups had the transgene insertion, producing eight different lines of 5-HT$_3$ transgenic mice. After a single cross with a non-transgenic (−/−)B6SJL/F1, mice positive for the transgene were bred to homozygosity (+/+) for the transgene by brother-sister mating. Further selection of the line to breed forward was done on the basis of the amount of receptor over-expression seen by (1) ligand binding and (2) receptor function as measured by a behavioral test for alcohol consumption (below). The 5-HT$_3$ transgenic mice described here appear to develop normally and have no overt abnormal physical or behavioral characteristics.

Protein expression

Figure 2:
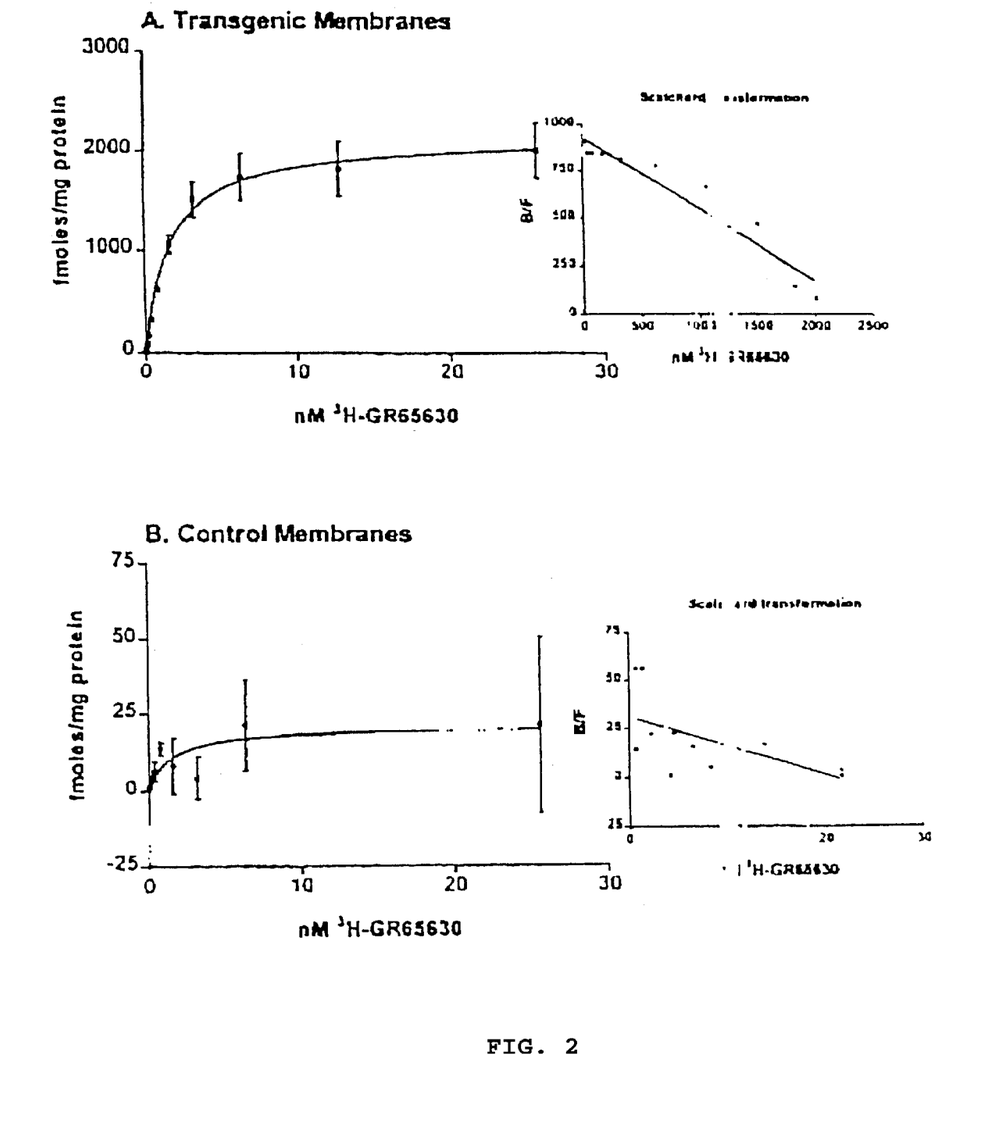
FIG. 2 shows homogenate binding with $^3\text{H-GR65630}$ in transgenic (A) and B6SJL/F1 control (B) mice cortical membranes. Transgenic membranes: $B_{max}$ =2155±129 fmol/mg. $K_D$=1.6±2.3,n=3, Hill no.=1.0, n=10. Control: $B_{max}$= 21±10 fmol/mg. $_1$K=1.6±2.3, n–3. Two-tailed unpaired t-test of x=3.368id7=22, P=0.0028.

5-HT$_3$ receptor expression was greatly increased in the transgenic mice cortical membranes as compared to control mice. Non-linear regression using GraphPad Prism software calculated a B$_{max}$ of 2155 fmol/mg protein an a $_D$K of 1.7 nM in cortical membranes from transgenic mice. The Hill plot gave a slope of 1.0, indicating a single site kinetics. Under the same conditions, binding in cortical membranes from non-transgenic B6SJL/F1 control mice yielded a B$_{max}$ of 21 fmol/mg protein and a K$_D$ of 1.6 nM was calculated (FIG. 2).

Figure 3:
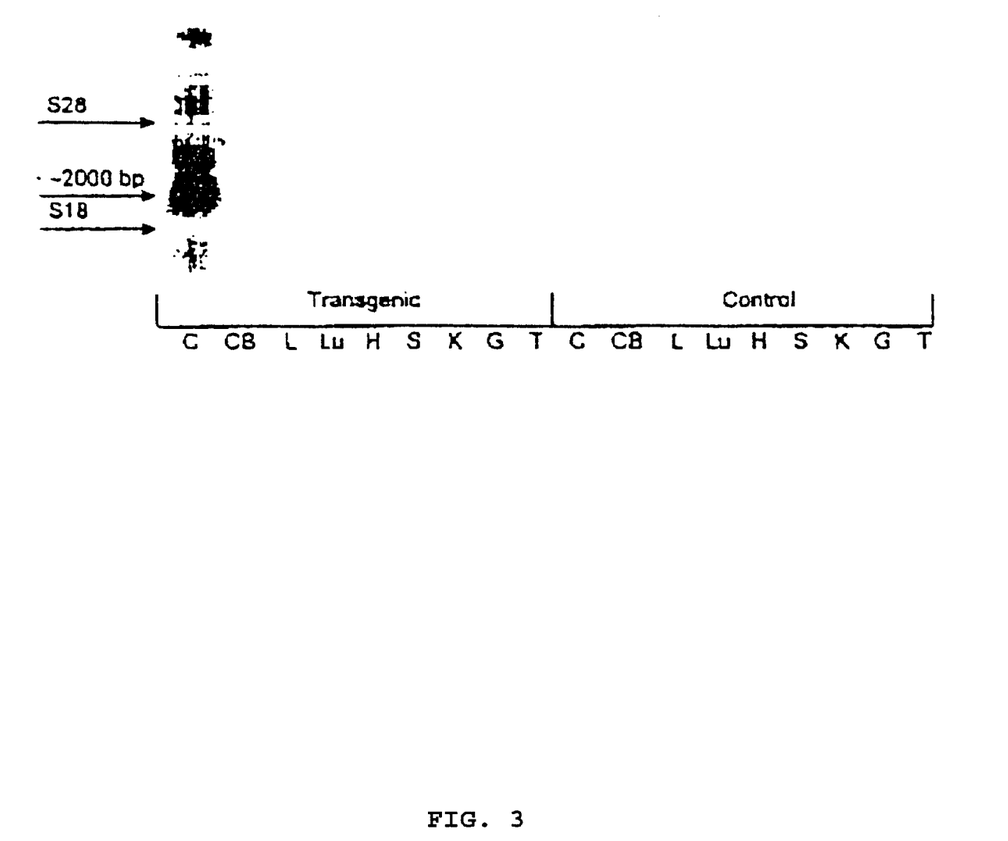
FIG. 3 shows representative northern analysis of various tissues from transgenic and B6SJL/F1 control mice. RNA 20 µg per well. C cortex, CB cerebellum, L liver, Lu lung, H heart, S spleen, K kidney, G small intestines, T testes.

Binding in membrane preparations from the cerebellum, liver, lung, heart, spleen, kidney, gut, testis, and skeletal muscle from transgenic mice were the same as those from non-transgenic transgenic B6SJL/F1 mice (see Table 1,infra). Lack of 5-HT$_3$ receptor over-expression in these tissues was confirmed by Northern analysis of RNA. Total RNA from cortex, cerebellum, liver, lung, heart, spleen, kidney, gut, testis, and skeletal muscle was extracted and identification of 5-HT$_3$ RNA was by a 32P-labeled probe for an 800 bp region of the 5-HT$_3$ cDNA. A prominent band of RNA that corresponded to the appropriate size (~2000 bp; see arrow in FIG. 3) was identified by this method from the cortex of the transgenic animals but not from any of the other tissues tested (FIG. 3).

Figure 4:
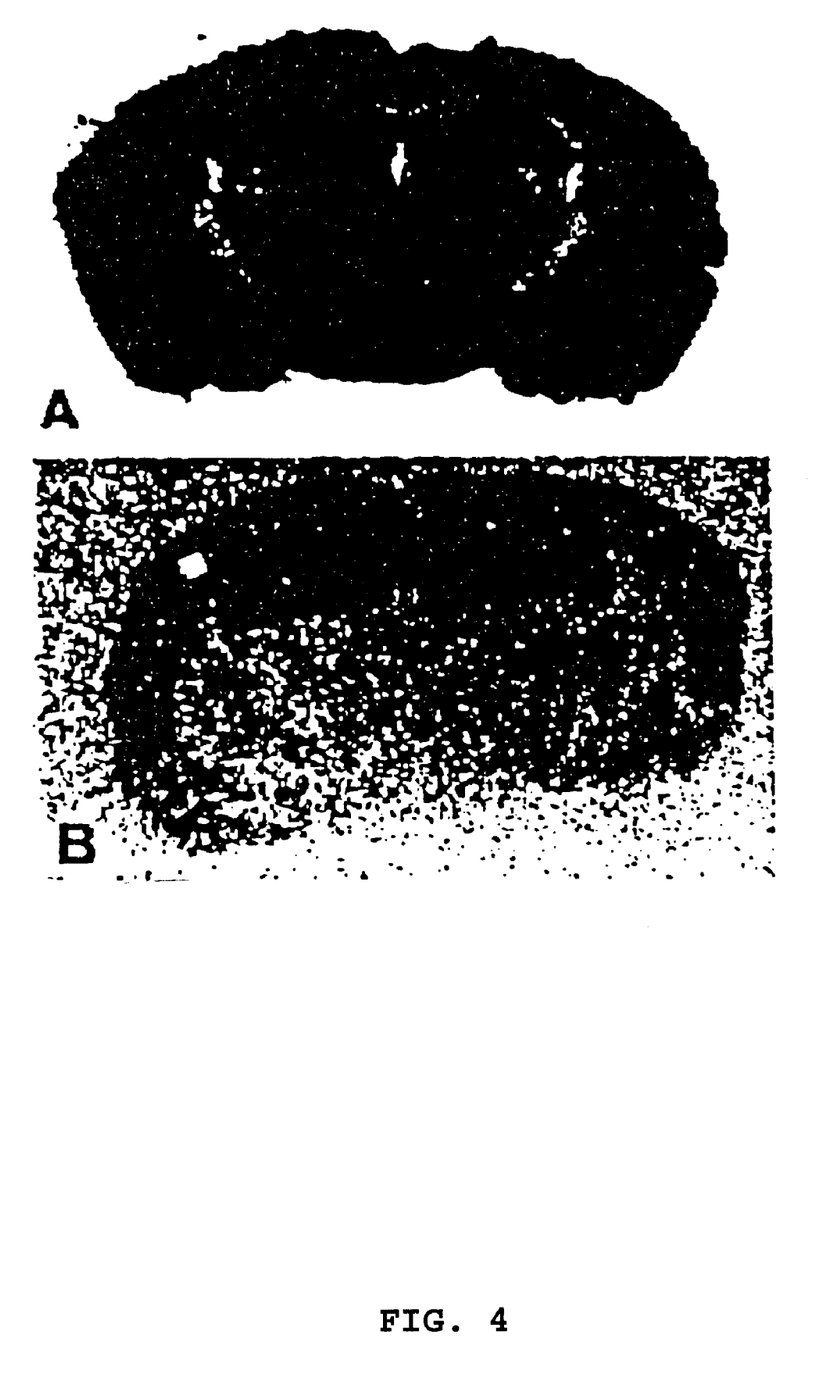
FIG. 4 is a $5\text{-}HT_3$ receptor binding with $^{125}\text{I-DAIZAC}$ (1 nM) in brain slices from transgenic (A) and B6SJL/F1 control (B) mice.

$^{125}$I-DAIZAC binding in brain slices showed receptor distribution in the forebrain. The receptor is expressed uniformly throughout the forebrain structures (FIG. 4) but not in cerebellum or brainstem. B6SJL/F1 control mouse brains show a similar receptor distribution in the cortex and hippocampus but a much lower receptor density. Thus, the promoter region used to produce this transgenic mouse was successful in limiting the expression of the receptor to forebrain areas.

TABLE 1

Specific binding (means ± SEM) with $^3$H-GR65630 in membranes from various tissues from transgenic and B6SJL/F1 control mice in fmol/mg protein, n.d., none detected, n = 2–4 group.

| Tissue | Transgenic | Control |
|---|---|---|
| Liver | n.d. | n.d. |
| Lung | 2.7 ± 4.1 | n.d. |
| Heart | 3.9 ± 1.8 | 0.25 ± 5.4 |
| Spleen | 8.2 ± 7.2 | 1.7 ± 3.9 |
| Kidney | 16.9 ± 8.0 | 3.9 ± 3.1 |
| Small intestines | 26.0 ± 7.7 | 26.6 ± 11.0 |
| Testes | n.d. | n.d. |
| Skeletal muscle | 8.0 ± 2.7 | 2.7 ± 0.4 |
| Cerebellum | 12.3 ± 14.9 | n.d. |
| Cortex | 969.6 ± 190.5 | 7.2 ± 2.9 |

Drinking behavior

Figure 5:
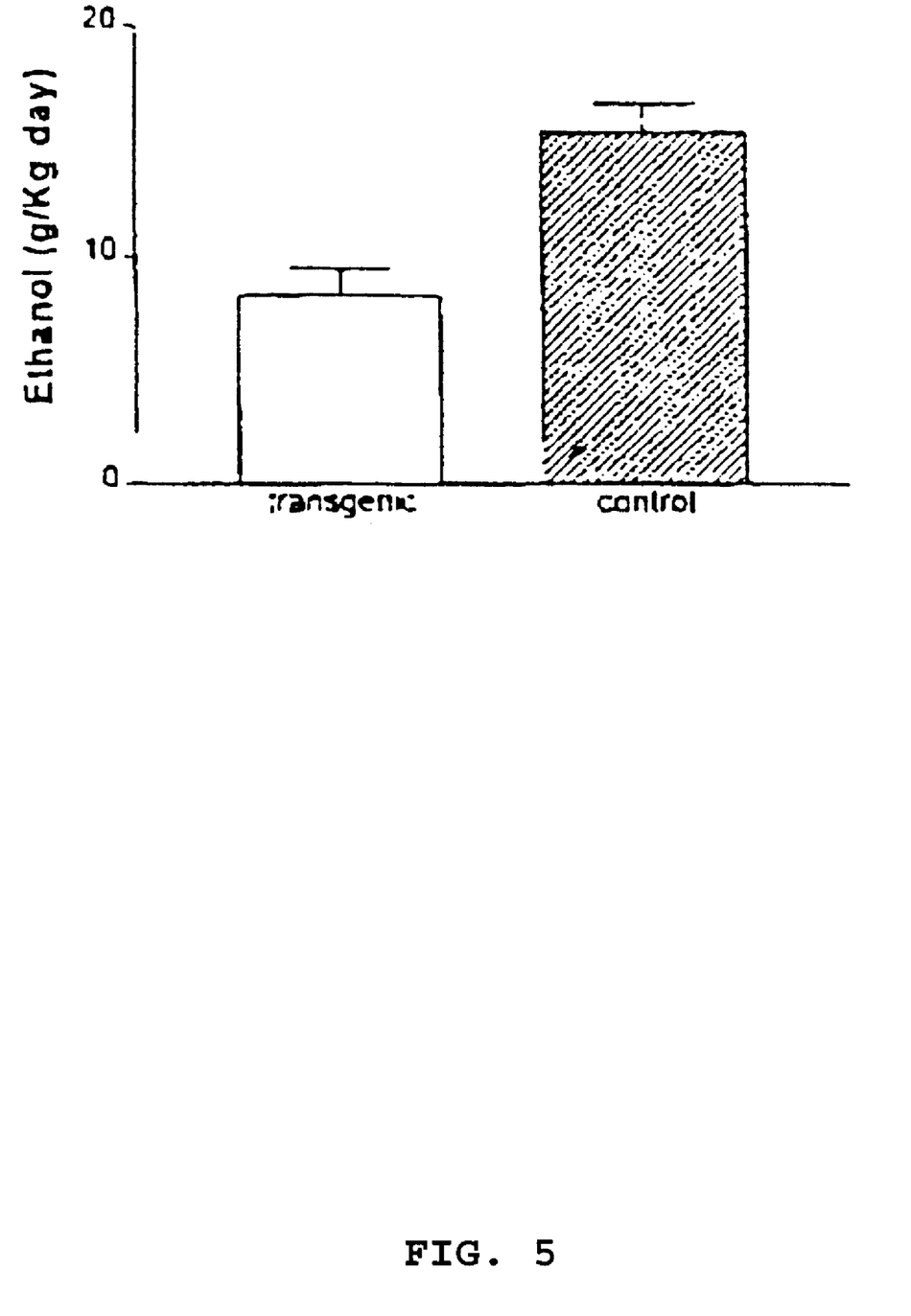
FIG. 5 shows ethanol consumption in transgenic and B6SJL/F1 control mice in a two-bottle choice test for 10 days, n=9 mice per group. Mean g/kg per day ethanol for transgenic group is 8.3±1.2 SEM and 15.4+1.3 SEM for controls. Two-tailed unpaired t-test (t=4.03; D7=16, P=0.00).

The 5-HT$_3$ over-expressing transgenic mice drank a means of 8.3 g/kg per day of ethanol as compared to 15.5 g/kg per day for the B6SJL/F1 control mice (FIG. 5). This decrease of 46% is significant to P=0.001 by Student's t-test. The controls drank 41% less water per day than the transgenic mice with the total fluid consumed per day remaining about the same for both groups (5.7 ml for transgenic mice and 5.8 ml for controls). The mean weight of the transgenic mice was 26.2 g compared to 25 g for controls, and this did not change significantly during the experiment.

The invention, as described and claimed herein, is applicable to both human and non-human mammals. If any claims are by law rendered unpatentable if construed to include human mammals, then the terms "mammal" or "mammals" as used herein shall refer only to a non-human mammal or mammals. Otherwise the term "mammal" in the claims refers to both human and non-human mammals.

What is claimed is:

1. A transgenic mouse whose genome comprises its endogenous 5-HT$_3$ gene encoding the 5HT$_3$ recetor and a transgene, wherein said transgene comprises a murine 5-HT$_3$ transgene operably linked to a rat CAM kinsas II$\mu$ promoter, wherein said 5-HT$_3$ transgene encodes the 5-HT$_3$ receptor, and wherein said mouse express said endogenous 5-HT$_3$ gene and the transgene, wherein the mouse is characterized by at least one characteristic selected from the group consisting of decreased craving for alcohol and decreased aggressiveness relative to non-transgenic mice of the parental strain.

2. The transgenic mouse of claim 1, wherein the 5-HT$_3$ transgene comprises a truncated 5-HT3 sequence.

3. The transgenic mouse of claim 1, wherein the 5-HT$_3$ transgene comprises a complete cDNA 5-HT$_3$ sequence.

4. The transgenic mouse of claim 1, wherein the expression of the transgenic 5-HT$_3$ receptor is limited to the central nervous system.

5. The transgenic mouse of claim 4, wherein the expression of the transgenic 5-HT$_3$ receptor is limited to the forebrain.

6. The transgenic mouse of claim 1, wherein the mouse is fertile and transmits the 5-HT$_3$ transgene to its offspring.

7. The transgenic mouse of claim 1, wherein the 5-HT$_3$ transgene has been introduced into an ancestor of said mouse at an embryonic stage.

8. A transgenic mouse whose genome comprises its endogenous 5-HT$_3$ gene encoding the 5-HT$_3$ receptor and a transgene, wherein said transgene comprise a murine 5-HT$_3$ transgene operably linked to a rat CAM kinase II$\mu$ promoter, wherein said 5-HT$_3$ transgene encodes the 5-HT$_3$ receptor, and wherein said mouse express said endogenous 5-HT$_3$ gene and the transgene, wherein the mouse is characterized by expression of at least a ten-fold increase in 5-HT$_3$ receptor in cortical membranes relative to non-transgenic mice of the parental strain.

9. The transgenic mouse of claim 8, wherein the 5-HT$_3$ transgene comprises a truncated 5-HT$_3$ sequence.

10. The transgenic mouse of claim 8, wherein the 5-HT$_3$ transgene comprises a complete cDNA 5-HT$_3$ sequence.

11. The transgenic mouse of claim 8, wherein the mouse is fertile and transmits the 5-HT$_3$ transgene to its offspring.

12. The transgenic mouse of claim 8, wherein the 5HT$_3$ transgene has been introduced into an ancestor of said mouse at an embryonic stage.

* * * * *

UNITED STATES PATENT AND TRADEMARK OFFICE
CERTIFICATE OF CORRECTION

PATENT NO. : 6,252,131 B1
DATED : June 26, 2001
INVENTOR(S) : Allan et al.

It is certified that error appears in the above-identified patent and that said Letters Patent is hereby corrected as shown below:

Title page, Item [54] and Column 1, line 1,
The title should read as follows:
-- [54] TRANSGENIC MAMMAL HAVING 5-HT$_3$ TRANSGENE OVEREXPRESSION IN THE CNS --.

Column 2,
Line 28, delete "$K_D$=1.6±2.3,n=3" and insert therefor -- $K_D$=1.7±0.4 nM --.
Line 29, delete "K=1.6±2.3,n=3" and insert therefor -- $K_D$=1.6±2.3, n=3 --.
Line 30, delete "x-3.368id7=22" and insert therefor -- $B_{max}$ values (t=-3.368;df=22) --.
Line 43, delete "D7=16" and insert therefor -- df=16 --.
Line 44, delete "P=0.00" and insert therefor -- P=0.001 --.

Column 7,
Line 10, delete "bp≡11 kbp" and insert therefor -- bp≅11 kbp --.

Column 8,
Line 29, delete MgC$_2$" and insert therefor -- MgCl$_2$ --.
Line 48, delete "72$\underline{20}$ C." and insert therefor -- 72º C --.

Column 9,
Line 30, delete "-700º C and insert therefor -- 72º C --.

Column 14,
Line 18, delete "kinase IIµpromoter" and insert therefor -- kinase IIα promoter --.

UNITED STATES PATENT AND TRADEMARK OFFICE
CERTIFICATE OF CORRECTION

PATENT NO. : 6,252,131 B1
DATED : June 26, 2001
INVENTOR(S) : Allan et al.

It is certified that error appears in the above-identified patent and that said Letters Patent is hereby corrected as shown below:

<u>Column 17,</u>
Line 13, delete "kinsas II$\mu$" and insert therefor -- kinase II$\alpha$ --.

<u>Column 18,</u>
Line 10, delete "delete "kinase II$\mu$" and insert therefor -- kinase II$\alpha$ --.

Signed and Sealed this

Twenty-seventh Day of August, 2002

Attest:

JAMES E. ROGAN
Attesting Officer *Director of the United States Patent and Trademark Office*